United States Patent [19]

Recktenwald et al.

[11] Patent Number: 4,704,891

[45] Date of Patent: Nov. 10, 1987

[54] METHOD AND MATERIALS FOR CALIBRATING FLOW CYTOMETERS AND OTHER ANALYSIS INSTRUMENTS

[75] Inventors: Diether J. Recktenwald; Rickie S. Kerndt, both of Cupertino; Michael R. Loken, Los Altos; Chia H. Chen, San Jose, all of Calif.

[73] Assignee: Becton, Dickinson and Company, Franklin Lakes, N.J.

[21] Appl. No.: 901,860

[22] Filed: Aug. 29, 1986

[51] Int. Cl.$^4$ ............................................ G06M 11/00
[52] U.S. Cl. .................................................... 73/1 R
[58] Field of Search ................ 73/1 R; 209/546, 576, 209/588, 587, DIG. 942; 356/243; 250/252.1, 573; 436/10; 424/7.1, 2, 3; 377/11

[56] References Cited

U.S. PATENT DOCUMENTS

| | | | |
|---|---|---|---|
| 3,412,037 | 11/1968 | Gochman et al. | 73/1 R |
| 3,791,517 | 2/1974 | Friedman | 209/546 |
| 4,135,821 | 1/1979 | Pechin et al. | 356/243 |
| 4,331,862 | 5/1982 | Ryan | 73/1 R |
| 4,380,392 | 4/1983 | Karabegov et al. | 356/243 |
| 4,434,647 | 3/1984 | Whitcomb et al. | 73/1 R |
| 4,438,390 | 3/1984 | Hogg | 377/11 |
| 4,596,464 | 6/1986 | Hoffman et al. | 377/11 |

Primary Examiner—Stewart J. Levy
Assistant Examiner—Robert R. Raevis
Attorney, Agent, or Firm—Richard J. Rodrick

[57] ABSTRACT

A method for calibrating an instrument for using that instrument to obtain at least one light-related signal from particles under analysis comprises directing an incident beam of light at calibration particles having one or more known characteristics related to the particles expected to be analyzed. Both a light signal and a noise signal from the calibration particles are detected. A measurement is made of the ratio of the detected light signal to the detected noise signal, and that measurement is reported. The measured ratio is then compared to a predetermined ratio which represents a threshold for minimum instrument performance. This method further includes adjusting, if the predetermined ratio has not been attained, the operation of the instrument, while the calibration particles are within the incident beam of light, until the measured ratio reaches the predetermined ratio whereby the instrument is calibrated for subsequently obtaining the light signal from particles to be analyzed. A kit of reagents for use in calibrating an instrument for performing two-color analysis of particles and particle standards for calibrating fluorescence analysis instruments are also part of the instant invention.

28 Claims, 10 Drawing Figures (a)  (b)  (c)  (d)

VOLUME RESULTS:

NOISE EVENTS: 93
MEAN CHANNEL: 140

OTHER RESULTS:

| PARAMETER | SIGNAL | NOISE | SEPARATION | MINIMUM | LOT ID |
|---|---|---|---|---|---|
| SSC | 192 | 16 | 176 | 160 | X1111H |
| FL1 | 190 | 38 | 152 | 140 | X2222J |
| FL2 | 140 | 43 | 97 | 90 | X3333O |

FL1 AVG: 32    FL2 AVG: 31    SSC AVG: 189

FL1 SIGNAL AVG: 114
FL2 SIGNAL AVG: 115
SSC SIGNAL AVG: 190

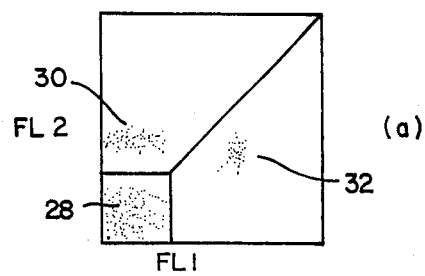
FL1 COMP: 39    FL2 COMP: 94
Fig. 4
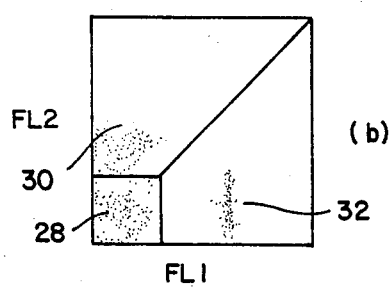
FL1 COMP: 0 ±5    FL2 COMP: 0 ±5

METHOD AND MATERIALS FOR CALIBRATING FLOW CYTOMETERS AND OTHER ANALYSIS INSTRUMENTS

BACKGROUND OF THE INVENTION

1. Field of the Invention

The present invention relates to a method for calibrating an instrument used to analyze particles, and more particularly, concerns a method and materials for calibrating flow cytometry instruments prior to using such instruments for obtaining at least one light-related signal from particles passing through the instrument.

2. Background Description

There are a number of commercially available instruments used for particle or cellular analysis. Characteristics of particles, particularly biological particles or cells, may be determined by techniques in which the particles remain relatively fixed while being analyzed or while the particles are moving in a stream or carried in a suspension. Flow cytometers are known and available for analyzing or detecting certain characteristics of particles which are in motion. In typical flow cytometry instruments, cells or other biological particles are caused to flow in a liquid stream so that each particle, preferably one at a time, passes through a sensing region which measure physical or chemical characteristics of the particles. Although a variety of signals may be detected for association with different characteristics of the particles, including electrical, acoustical and radioactive, flow cytometers commonly rely on optical signals for the analysis of particles passing through the instrument. In any event, whether the analysis instrument is used to analyze particles in a static or dynamic state, preliminary set-up steps are normally required in preparing the instrument for use. Insofar as cells or other biological particles are very small and the signals to be detected with respect to those particles are often at a low magnitude, proper calibration of the instrument, prior to conducting the analysis, is desirable to assure reliable test results.

Current techniques for calibrating instruments useful for biological particle or cellular analysis are highly operator dependent. In other words, the operator's judgment and experience is called upon during the calibration procedures for adjusting the controls, establishing proper thresholds and maintaining a set of standards for the particular tests to be conducted. Indeed, while experienced operators are quite capable of properly calibrating an instrument prior to use, much guesswork and speculation is used by such an operator to sense that proper calibration has been attained. For instance, in aligning various optical elements of an instrument, such as a flow cytometer, the person doing the calibration typically views a screen or a CRT and, by eyeball judgment, in conjunction with adjustment of various controls, determines that the instrument has been calibrated. Of course, in employing the typical eyeball calibration techniques, reproducibility of test results could be compromised.

Flow cytometers and other biological particle analysis instruments are normally calibrated with particles which simulate or approximate the types of particles or cells which are expected to undergo actual analysis. Thus, calibration particles should be selected so that they have characteristics similar to the particles to be tested for, such as size, volume, surface characteristics, granularity properties, color features (cellular stains, dyes, immunofluorescent tags and the like). Past and current calibration procedures for flow cytometry instruments include the utilization of chicken red blood cells for the calibration steps. While chicken red blood cells are reliable for some aspects of the calibration procedures, they, nevertheless, are not entirely satisfactory, particularly because of spectral deficiencies in some light-related characteristics. In addition to biological samples for calibration purposes, microspheric beads have become available for calibrating cellular analysis instruments. For example, beads made out of latex material for use in calibrating a particle counting instrument were described in U.S. Pat. No. 4,331,862. Calibration beads specifically directed for calibrating flow cytometry instruments are commercially available from the Flow Cytometry Standards Corporation, Research Triangle Park, N.C.

Even though the availability of calibration beads has led to improvements in the calibration techniques of particle analysis instruments there is still a substantial amount of operator guesswork in determining when the instrument has been properly calibrated. Accordingly, there is still a need and desire to establish calibration procedures which not only provide reproducible test results, but also eliminate the speculation and guesswork attendant to currently utilized calibration techniques. It is toward the fulfillment of such improvements that the present invention is directed.

SUMMARY OF THE INVENTION

The method of the present invention for calibrating an instrument for using that instrument to obtain at least one light-related signal from particles under analysis comprises directing an incident beam of light at calibration particles having one or more known characteristics related to the particles expected to be analyzed. Both a light signal and a noise signal from the calibration particles are detected. Preferably, the light signal is detected from one type of particle in the calibration mix, such as a fluorescent particle, and the noise signal is detected from another type of particle in the calibration mix, such as a non-fluorescent particle. A measurement is made of the ratio of the detected light signal to the detected noise signal, and this ratio is reported. The measured ratio is compared to a predetermined ratio which represents a threshold for minimum instrument performance. This method includes adjusting, if the predetermined ratio has not been attained, the operation of the instrument, while the calibration particles are within the incident beam of light, until the measured ratio reaches, or exceeds, the predetermined ratio whereby the instrument is calibrated for subsequently obtaining the light signal from particles to be analyzed.

In a preferred embodiment of this aspect of the invention, the method is employed for calibrating a flow cytometry instrument and includes passing calibration particles, having known characteristics related to the particles expected to be tested, in a liquid flow stream so that each calibration particle passes, substantially one at a time, through an incident beam of light. Both a light signal and a noise signal relating to the calibration particles are detected and the signal to noise ratio is determined. This ratio is reported as a measured separation value between the light signal and the noise signal. The measured separation value is compared to a predetermined separation value representative of a threshold for minimum instrument performance. Adjustment of the operation of the instrument is performed, if the predetermined separation value has not been attained, until the measured separation value reaches the predetermined separation value whereby the instrument is calibrated for subsequently obtaining light signals from particles to be analyzed.

Another aspect of the present invention is a kit of reagents for use in calibrating an instrument for performing two-color fluorescence analysis of particles. The kit comprises a first container having calibration particles therein capable of emitting fluorescence at a first wavelength. A second container includes calibration particles capable of emitting fluorescence at a second wavelength. A third container has calibration particles therein substantially incapable of emitting fluorescence. This kit or reagents is suitable for use in the above-described method for calibrating a flow cytometry instrument.

A further aspect of the present invention relates to particle standards, for calibrating fluorescence analysis instruments, comprising osmium tetroxide-fixed chicken red blood cells, which are incapable of emitting fluorescence, including autofluorescence, until reacted with a specific fluorophore.

In accordance with the principles of the present invention, calibration methods and materials provide substantial improvements over currently known and used calibration techniques. The present invention allows the operator to calibrate a particle analysis instrument by relying on calibration standards and/or thresholds which have been predetermined and are made available to the operator. Preferably, the threshold values for establishing minimum performance of the instrument are displayed to the operator during the calibration procedures so that a calibration target is known. By adjusting and tuning the features of the instrument until the threshold values are attained, the operator is assured that the instrument is correctly functioning for the tests to be performed. Guesswork and eyeballing techniques of calibration are eliminated by the calibration procedures of the present invention so that calibration errors are reduced or eliminated, and reproducibility of tests is enhanced. The calibration procedures of the present invention are particularly suitable for flow cytometry instruments since proper calibration assures proper alignment of the optical features of the instrument, accounts for spectral cross-talk by employment of compensation techniques, and provides information to the operator about the sensitivity of the instrument particularly for optimizing the performance of the instrument for immunofluorescent analysis of particles. It should be pointed out that the advantages and features of the present invention extend beyond flow cytometry instruments, and may be utilized in other analysis instruments such as automated microscopes, fluorescence microscopes, quantitative microscopes, image analyzers, and the like.

BRIEF DESCRIPTION OF THE DRAWINGS

FIG. 1(a) through FIG. 1(d) are graphical displays of histograms illustrating number of events (counts) versus channels for the four parameters of volume, side scatter, fluorescence color 1 and fluorescence color 2, respectively.

FIG. 2(a) is a dot population graphical display of two color fluorescence analysis (FL 2 vs FL 1), and FIG. 2(b) is a dot population graphical display of side scatter versus fluorescence analysis.

FIG. 3(a) is a dot population graphical display of two color fluorescence analysis (FL 2 vs FL 1), and FIG. 3(b) is a dot population graphical display of side scatter versus volume analysis; FIG. 4(a) is a dot population graphical display of two color fluorescence analysis (FL 2 vs FL 1) illustrating uncompensated fluorescence analysis; FIG. 4(a) also displays the mean channel difference between the unstained population and the stained population for fluorescence color 1 (FL 1); FIG. 4(b) is a dot population graphical display of two color fluorescence analysis (FL 2 vs FL 1), illustrating compensated fluorescence analysis; FIG. 4(b) also displays the mean channel difference between the unstained population and the fluorescence color 2 population (FL 2) after compensation has occurred.

DETAILED DESCRIPTION

Figure 1:
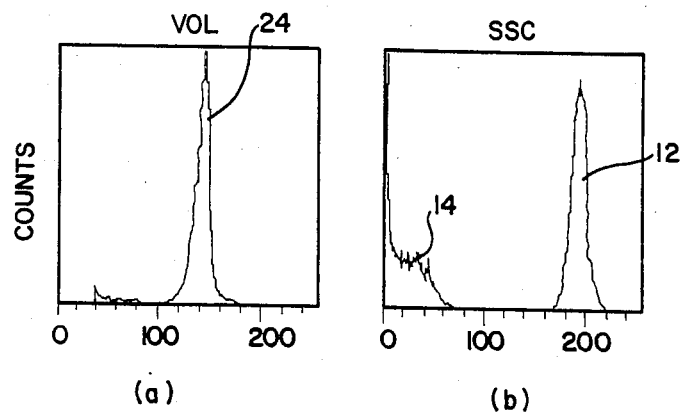
FIG. 1 also illustrates volume results relating to noise events and mean channel statistics and signal, noise, separation and minimum values on the mean channel scale for side scatter, fluorescence color 1 and fluorescence color 2.
Figure 1:
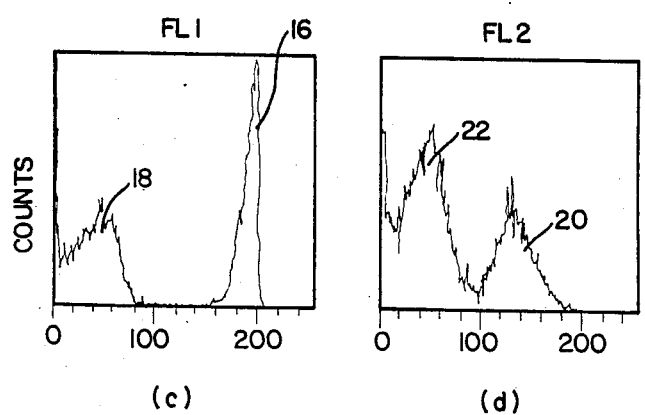

While this invention is satisfied by embodiments in many different forms, there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be measured by the appended claims and their equivalents.

Figure 3:
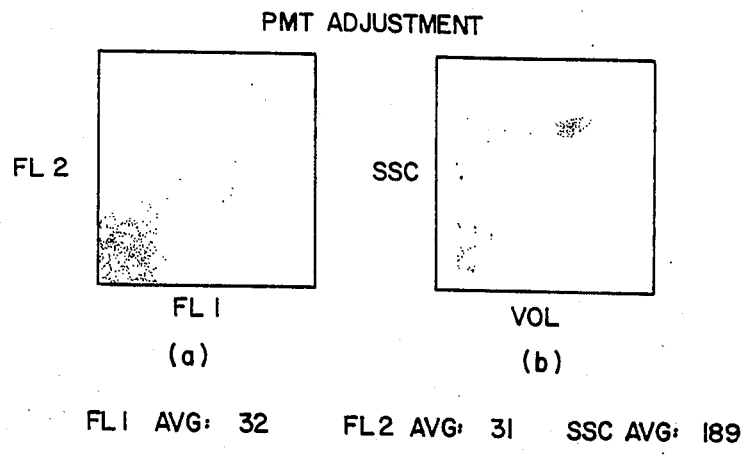
FIG. 3 further displays the channel averages for the populations of fluorescence color 1 (FL 1), fluorescence color 2 (FL 2) and side scatter (SSC) for photomultiplier tube (PMT) adjustment of the instrument.
Figure 2:
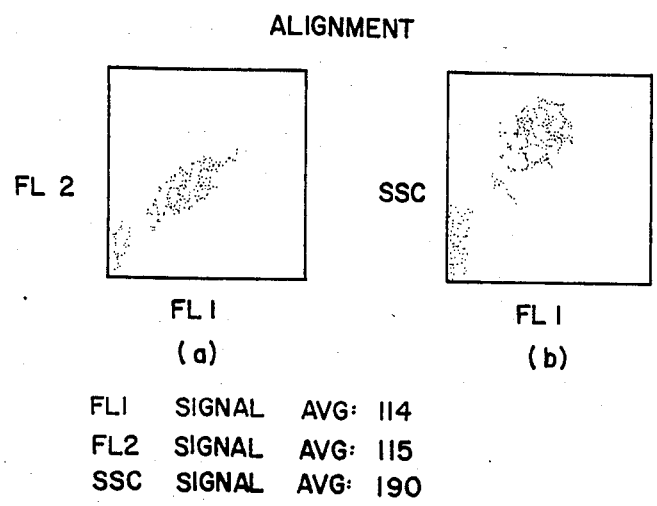
FIG. 2 also displays the channel averages for instrument alignment purposes.

Before turning directly to the drawings, it should be pointed out that the calibration technique to be described below, and in conjunction with the drawings, is associated with a flow cytometry instrument. Specifically, the exemplary calibration procedures to be described are associated with a FACS ™ analyzer marketed by Becton Dickinson Immunocytometry Systems, Mountain View, Calif. The histogram display of FIG. 1 and the dot population displays of FIGS. 2–4 are typical displays seen on the screen of the FACS analyzer during the calibration procedures. Appropriate software to carry out the calibration procedures, according to the principles of the present invention, may be provided for the flow cytometry instrument to facilitate the various calibration procedures and functions.

Briefly, the flow cytometry instrument to be calibrated includes a nozzle or like device for providing a liquid flow stream of particles to be analyzed. Typically, the liquid flow stream of particles is ensheathed in a sheath fluid so that the particle stream may be hydrodynamically focused as it flows through an incident beam of light normally directed at right angles to the stream of particle flow. As these particles pass through the beam of light, light characteristics associated with each particle may be detected. Therefore, one or more light detectors for measuring fluorescence, light scatter (in one or more directions), absorbance and the like may be included. These light detectors include photomultiplier tubes (PMT's) which convert light signals to electrical signals. In addition to detecting light associated with the particles, an electrical impedance measurement may also be taken as the particles pass through an orifice. This impedance measurement is related to particle volume and is based on the well-known Coulter principle. In the FACS analyzer, whose calibration will be described below, PMT's are provided for detecting two different colors of fluorescence and light scatter, in this instance side scatter, for measuring scatter from the particles at substantially 90° with respect to the incident beam of light. The FACS analyzer further provides for the measurement of electrical impedance associated with particle volume. Thus, four different parameters or characteristics of the particles may be detected or measured, all of which should be calibrated prior to using the instrument to measure these characteristics of particles from the sample to be tested.

The calibration techniques of the present invention are intended to inform the operator of the instrument that the instrument is calibrated based on predetermined threshold values representative of minimum instrument performance. These minimum threshold values provide an indication of sensitivity of the instrument for carrying out particle analysis, particularly immunofluorescent performance. For example, in addition to side scatter and volume, the specific flow cytometry instrument being described is capable of detecting two different colors of fluorescence, for a total of four different parameters. For purposes of the ensuing discussion, and for exemplary purposes only, the first fluorescence color of particles to be analyzed will be in the green spectral region associated with particles labeled with fluorescein representing FITC stained cells; the second fluorescence color of particles to be analyzed will be in the red spectral region associated with phycoerythrin labeled particles representing PE stained cells. Of course, other fluorochromes or labeling agents may be employed, if desired, depending upon the tests to be conducted and the particles or cells to be analyzed.

When the operator turns the instrument on in preparation for the prescribed tests, for example at the beginning of the day, the optical elements of the instrument could be out of alignment. If the tests to be performed relate to data acquisition for monitoring particles of the immune system, such as leucocyte samples, the operator may desire to determine whether the instrument is calibrated to the proper sensitivity for conducting these tests. Instrument sensitivity performance and the results provided thereby are illustrated in FIG. 1. In describing the specifics of FIG. 1, it is understood that the sensitivity test is merely a confirmatory test to determine whether the instrument is properly calibrated for analyzing certain types of particles, such as leucocytes or other immune system cells or particles. If the results of the sensitivity tests indicate that the threshold values for minimum performance of the instrument are met, the instrument is deemed to be properly calibrated and no further adjustments, alignments or tuning of the instrument will be required to subsequently operate the instrument for the particle analysis. However, since some tuning and adjustments are normally required to calibrate the instrument for reliable performance, the operator may desire to undertake the adjustment and calibration steps, explained in conjunction with FIGS. 2–4 below, prior to determining sensitivity in conjunction with the displays of FIG. 1. In the ensuing discussion, the sensitivity determination and the techniques to accomplish same will first be described together with the displays of FIG. 1.

To initiate this procedure, the operator employs the calibration particles of the present invention. A reagent kit is provided which preferably includes three containers, each having different plastic microspheres or beads therein. In the preferred form, the different beads are maintained in phosphate buffered saline (PBS) containing gelatin, 0.1% TWEEN 20 (a trademark of Atlas Chemical Industries, Inc. for a general purpose emulsifier and surface active agent) and 0.1% sodium azide as a preservative. Fluorescein labeled (FITC) beads, at approximately 5 microns diameter, are provided in the first container. Phycoerythrin labeled (PE) beads, at approximately 5 microns diameter, are provided in the second container. Unlabeled beads, at approximately 4.5 microns diameter, are included in the third container. The concentration of the beads in each of the three containers is approximately $10^6$ particles per milliliter. A sample tube is prepared by the operator by mixing the FITC, PE and unlabeled beads in a 1:1:1 ratio by adding one drop of each of the three reagents to three milliliters of sterile PBS. This sample tube with the mixture is then inserted into the FACS analyzer, which is operated in known fashion so that the beads pass substantially one at a time through an incident beam of light.

In addition to detecting signals related to volume, light scatter and both fluorescence determinants, noise signals for each parameter are also detected by the instrument. FIG. 1 represents the display on the instrument screen of the four parameters provided in the form of a histogram. The Y axis of the histograms are particle counts and the X axis is the number of electrical channels over which data acquisition is made. In the embodiments being described, there are 255 channels represented along the X axis of the various histograms. It is preferred that the histograms be reported or displayed in a log scale relationship so that the separation of histogram peaks between noise and signal is seen as a difference, but is actually expressed as a linearized ratio.

More specifically, the light-related signals are displayed in FIGS. 1(b),(c) and (d) relating to side scatter, FITC and PE, respectively. Looking first at FIG. 1(b), the side scatter signal is illustrated by curve 12, whereas noise is illustrated in region 14. Similarly, in FIG. 1(c), FITC signal is illustrated by curve 16, whereas noise is illustrated in region 18. In FIG. 1(d), PE signal is illustrated by curve 20, while noise is indicated within region 22. With respect to volume displayed in FIG. 1(a), the volume signal is displayed under curve 24; noise detection is displayed below the histograms as the number of noise events.

It can be seen with respect to the light-related signals of scatter and fluorescence, namely FIGS. 1(b),(c) and (d) that there is a separation or difference between the peaks of the actual light signal and the noise signal. As mentioned above, although this separation between signal and noise is preferably calculated on a log scale, the ratio of signal to noise is expressed as a linear difference on the X axis of the histograms. Therefore, when viewing the histograms, one can readily discern the spacing or separation between peaks of the signal and the noise with respect to scatter, FITC and PE.

In the histograms of FIGS. 1(c) and (d) for the fluorescence analysis, what is actually being measured is the amount of separation between average fluorescent intensity of labeled compared to unlabeled beads, as provided by the aforementioned reagents. Therefore, in FIG. 1(c), curve 16 represents the average fluorescence intensity of those beads labeled with FITC, whereas curve 18 represents the intensity of noise as a result of the unlabeled beads in the reagent mixture used for calibration purposes. Similarly, in FIG. 1(d), curve 20 represents the average fluorescence intensity of beads labeled with PE, while curve 22 represents the average intensity of noise from the unlabeled beads provided by the reagent mixture for calibration. Thus, by providing a single reagent mixture of equal ratios of beads labeled with FITC, with PE, and unlabeled beads, calibration of the instrument may be readily achieved for two color fluorescence analysis.

With respect to the side scatter signal as represented by FIG. 1(b), noise is actually introduced so that a separation value between noise and signal may be measured. This is necessary because the noise represented by region 14 of FIG. 1(b) does not result from unlabeled cells as occurs in the fluorescence signal. In this Figure, side scatter (SSC) noise is triggered on an unrelated signal to generate a reference signal for noise. Accordingly, the FL 2 signal is arbitrarily chosen to generate a reference signal. Noise is introduced into the side scatter signal by adjusting the FL 2 controls on the flow cytometry instrument so that the event rate (or flow rate of particles) through the instrument is about double the event rate for obtaining data with respect to volume, FL 1 and FL 2. By this expedient, noise occurs in the side scatter signal so that the linearized amount of separation between the noise and scatter signals may be determined.

In addition to the graphic displays preferably provided in histogram form, the screen of the instrument being calibrated may be programmed to display the results in the form of a digital readout. Software for the instrument, including calibration procedures, may be readily programmed to provide information relating to the accumulated data. Therefore, it can be seen on FIG. 1, below the histograms, that volume results are reported in digital readout form so that noise events and mean channel signal may be read by the operator. In calibrating an instrument such as a FACS analyzer, the volume mean channel should be approximately midscale in the volume histogram. A mid-scale reading indicates that the orifice through which the particles flow is correctly installed in the instrument and that the volume controls on the instrument are properly set. A noise event level preferably below 500 events is indicative of proper set up of the instrument.

FIG. 1 also displays on the screen the digital readings associated with the respective histograms of FIGS. 1(b),(c) and (d). The various parameters of SSC, FL 1 and FL 2 are listed along with readings for signal, noise, separation, minimum and lot ID. Lot ID and minimum values are related to each other. Prior to inserting the mixture of calibration beads into the instrument, the operator is instructed to feed the lot ID number into the program for regulating the calibration procedures. Since the calibration beads may have variable properties including different fluorescence brightness, intensity and the like, calibration of the instrument should take into account these variable properties. Thus, depending upon which calibration beads, identified by lot ID number, are being used, different predetermined separation values are established as minimum or threshold values for minimum instrument performance. Since the software may be preprogrammed, the predetermined minimum separation value is established for display on FIG. 1 as long as the lot ID number has been fed into the program by the operator at the outset of the calibration procedures.

Displayed at the bottom of FIG. 1 are the average mean channel values for signal and noise for side scatter, FL 1 and FL 2, associated with the histograms of FIGS. 1(b),(c) and (d), respectively. For example, the side scatter signal is displayed as having a mean average channel at 192, while the mean average channel for noise is at 16. The separation between these signal and noise results is reported at 176. The predetermined minimum separation value for side scatter signal is reported at 160. This minimum side scatter separation value is the desired level for the instrument to be sufficiently calibrated for reliably making side scatter measurements. Therefore, since the actual measured separation is at 176, the minimum is exceeded. Accordingly, the instrument is deemed to be calibrated for subsequent tests of particles in which side scatter is a signal to be detected.

Digital displays of the mean average channel for signal, noise and separation are also provided for the FL 1 and FL 2 signals. As illustrated in the example of FIG. 1, the separation values for FL 1 and FL 2 both exceed the minimum separation values, so that the operator may readily conclude that the instrument is properly calibrated for these two signals. The software for the above-described calibration procedure calculates a signal to noise ratio on a log scale, but expresses the ratio on a linearized basis which makes the peaks on the screen appear spaced apart from each other and therefore convenient to interpret. In the event that any or all of the light-related signals of scatter and fluorescence have measured separation values which are below the predetermined minimum, then further adjustments of the instrument should be considered for proper calibration. FIGS. 2,3 and 4 illustrate the screen displays of the FACS analyzer instrument in performing these calibration adjustments for aligning the optical elements for optimizing instrument performance, undertaking PMT adjustments and compensating for spectral cross-talk or overlap for two-color fluorescence analysis of particles.

In adjusting the instrument to assure that the optical elements are properly aligned for optimum performance, calibration may be performed by using the FITC labeled beads from the first container of the reagent kit described above. A tube of FITC labeled bead suspension may be prepared by adding one drop of FITC bead reagent to 1 milliliter of sterile PBS. This tube is then inserted into the FACS analyzer, and in conjunction with the calibration software, the screen displays dot population plots as illustrated in FIG. 2. FIG. 2(a) illustrates FL 2 vs FL 1, whereas FIG. 2(b) illustrates side scatter (SSC) vs FL 1. Below the dot plots is displayed digital information relating to the channel averages for the signals of FL 1, FL 2 and SSC. Referring first to FIG. 2(a), calibration is attained when the dot population for the green (FITC) beads is located near the center of the display. The fluorescence PMT voltages (on the instrument) may be adjusted to move the dot population to this location. With respect to the FL 1 and FL 2 signal averages, printed below the dot plots, the operator assures calibration by maximizing these signals. Optical elements of the instrument, such as the condenser lens controls, are turned or adjusted to maximize these signal averages, which should be maximized at approximately the same time. When near the maximum, the dot population displayed in FIG. 2(a) is made as tight as possible by the operator. With respect to FIG. 2(b), and the SSC signal average displayed below the dot plots, a target value, normally predetermined, is the goal for calibration. For example, for the FACS analyzer instrument, the target for the SSC signal channel average is about 190. To achieve this target, the operator may adjust the side scatter (SSC) PMT voltage on the instrument until the SSC signal average reaches approximately 190. Other adjustments of the optical elements or PMT's may be needed to achieve the target level for the SSC signal average. Both the dot plot populations and the digital readout numbers assist the operator in calibrating the instrument for proper optical alignment.

In similar fashion to optical alignment, the photomultiplier tubes (PMT's) may also be adjusted during theoth the dot plot populations and the digital readout numbers assist the operator in calibrating the instrument for proper optical alignment.

In similar fashion to optical alignment, the photomultiplier tubes (PMT's) may also be adjusted during the calibration procedures. FIG. 3 illustrates typical dot plot populations associated with PMT adjustment. FIG. 3(a) is a dot plot of FL 2 vs FL 1, whereas FIGS. 3(b) is a dot plot of side scatter (SSC) vs volume. In determining whether PMT adjustment should be made, the operator employs a different calibration particle procedure from those described above. In this instance for PMT adjustment, the operator preferably prepares a tube of unlabeled bead suspension by adding one drop of unlabeled beads, from the unlabeled bead container of the above-described reagent kit, to one milliliter of sterile PBS. This tube of unlabeled beads is then inserted into the FACS analyzer, and in conjunction with the software for calibration, the screen displays dot plot populations as illustrated in FIG. 3. In addition to the dot plots, FIG. 3 also displays three numbers representing the channel mean averages for the populations of the three parameters of FL 1, FL 2 and SSC. While the calibration particles are flowing through the instrument at a controlled, known rate, the operator aims at a predetermined target for values of FL 1 average, FL 2 average and SSC average. For both FL 1 and FL 2 averages, the predetermined target may be set at a level of 30, for example, and if that level is not attained, the operator may adjust the respective fluorescence 1 or fluorescence 2 PMT voltage controls on the instrument until the channel mean for FL 1 or FL 2 displayed on the screen is set as close to 30 as possible. In similar fashion, the target for SSC average may, for example, be set at 190. If this level is not displayed at first, the operator may adjust the light scatter PMT voltage control on the instrument until the channel means for SSC displayed on the screen is set as close to 190 as possible. Of course, it is understood that these average values are meant for exemplary purposes, and may vary according to instrument design, tests to be performed, or other factors. If acceptable values for the channel means cannot be achieved, the operator may have to return to the alignment procedures for the instrument described in conjunction with FIG. 2.

Having adjusted the PMT's and performed alignment of the optical elements of the instrument, another adjustment may be made in establishing the calibration of the instrument. This additional adjustment relates to compensation for spectral cross-talk or overlap in the event that two-color fluorescence analysis is to be performed. This procedure facilitates the adjustment for fluorescence compensation so that undesired green signal will be removed from the red (PE stained) population, and undesired red signal will be removed from the green (FITC stained) population.

To perform the fluorescence compensation procedures, the operator preferably starts with a tube of calibration particles similar to that prepared with respect to the sensitivity test described above. This tube is prepared with a 1:1:1 mixture of FITC, PE and unlabeled beads by adding one drop of each of the three reagents, from the above-described containers, to three milliliters of sterile PBS. When this tube is inserted into the analyzer instrument, and in conjunction with the software program for calibration procedures, the screen displays a real-time dot plot, representing uncompensated fluorescence, such as seen in FIG. 4(a). The three separate dot populations displayed in FIG. 4(a) represent the unstained, green and red stained calibration beads. Unstained beads are typically located inside the square in the lower left corner of the display, illustrated by region 28. Red (PE stained) beads are typically located above the unstained population, indicated by region 30. The green population is to the right of the unstained population, indicated by region 32. Until fluorescence compensation is provided for on the instrument, the location of regions 28, 30 and 32 are only approximate. Below the dot plot of FIG. 4(a) is a digital display of FL 1 compensation and FL 2 compensation. If these digital values are not fluctuating at or close to zero, adjustments should be made for fluorescence compensation.

Compensation is provided for two-color fluorescence analysis by adjusting FL 1 compensation and FL 2 compensation controls on the instrument until the compensation values listed on the screen are as close to zero as possible. After adjustment is made, the compensation value should fluctuate and vary equally above and below zero. With respect to FL 1 compensation, the compensated value represents the difference between the mean horizontal channel for the unstained population and the mean horizontal channel for the green stained population. As the FL 1 compensation control is adjusted on the instrument and the value on the screen approaches zero, the green population 32 on the dot plot should move downwardly until it is even with the unstained population 28 on a horizontal line parallel to the horizontal axis, as seen in FIG. 4(b).

In similar fashion, the mean channel difference listed next to FL 2 compensation on the screen represents the difference between the mean vertical channel for the unstained and red stained populations. As the FL 2 compensation control is adjusted on the instrument and the value on the screen approaches zero, the red population 30 on the dot plot should move horizontally until it is even with the unstained population 28 on a vertical line parallel to the vertical axis, as illustrated in FIG. 4(b). These adjustments of the FL 1 and FL 2 controls achieve fluorescence compensation by electrically subtracting a proportion of the unwanted green signal from the red population, and by electrically subtracting a proportion of the unwanted red signal from the green population. Compensation is achieved when the predetermined values of fluorescence compensation on the screen, set by the computer program at zero, are met. If acceptable or target settings cannot be achieved, the operator may be required to return to the alignment and PMT adjustment procedures as explained above.

Once alignment, PMT adjustment and fluorescence compensation have been completed, the operator may return to the sensitivity test described above in conjunction with FIG. 1. If the minimum separation values are achieved for each of the parameters being calibrated, the operator can proceed to use the instrument with full reliance that it is properly calibrated for the tests to be conducted.

Regarding the calibration particles to be utilized for the instantly described calibration procedures, a variety of particles may be used as standards. For instance, biological samples such as particles or cells may be employed as long as these samples either have, or may be treated to have, characteristics similar to the actual particles to undergo analysis. Along these lines, chicken red blood cells may be employed with proper selection techniques. A modified form of chicken red blood cells may be used as particle standards. Specifically, fluorescently labeled osmiumtetroxide-fixed chicken red blood cells may serve as particle standards since they have the size and scatter properties of biological cells. Moreover, osmiumtetroxide fixation quenches the autofluorescence of cells. These cells may be biotinilated, and subsequently reacted with a fluorophore conjugated to avidin in known fashion. Fluorescence of the avidin complex, bound to the cells, is not quenched by the osmiumtetroxide on the cells. The specific fluorophore conjugated to the avidin has spectral properties characteristic for cell-surface staining. Many different fluorophores may be used in the conjugates, including those to be described below.

The most preferred type of calibration particles for the present invention are plastic microbeads. Such beads may be fabricated with substantially uniform diameter, and have surface characteristics which are suitable for surface binding of fluorophores or other colorimetric marking agents. Substantially spherical beads may be formed having a diameter between 0.5 and 20 microns, and most preferably between 2 and 8 microns, so that these calibration beads are of the same order of magnitude in size as leucocytes. While the beads are usually made in solid form, they may be hollow inside and could be vesicles, such as liposomes or other microcarriers. Moreover, the beads do not have to be perfect spheres in order to function in accordance with the present invention. Plastic materials such as polystyrene, polyacrylamide and other latex materials may be employed for fabricating the beads, and other plastic materials such as polyvinylchloride, polypropylene and the like may also be utilized. Besides the fluorescein and the phycoerythrin labels for the beads described above, other fluorescence labels, such as allophycocyanin, Texas red, rhodamine, rhodamine-type compounds and other stains may be employed as fluorescent labels for purposes of the present invention. In preparing a kit of these reagents for calibration of instruments, the beads, whether labeled or unlabeled, are preferably provided as an aqueous solution so that the beads are present in concentrations ranging from $10^5$ to $10^8$ particles per milliliter, and preferably having a concentration of at least $10^6$ particles per milliliter.

While the calibration procedures were described above with specific reference to a flow cytometry instrument, no such limitation is intended for the present invention. Indeed, the calibration procedures of the present invention are applicable to instruments which analyze non-moving particles as well as moving particles. Various microscopes, such as fluorescence, automated, and quantitative microscopes, as well as image analyzers may be calibrated in accordance with the present invention.

Thus, the present invention provides a method and materials for calibrating an instrument prior to using that instrument for obtaining at least one light-related signal from particles under analysis. The present invention may be used with appropriate software to display minimum values of signal to noise ratios which should be met in order to determine that the instrument is calibrated for a specific light-related parameter. By reporting the signal to noise ratio as a differential on the linear scale, operator convenience is not only facilitated, but guesswork, eyeballing and errors are substantially reduced or eliminated. The techniques and materials of this invention also provide quality assurance for clinical diagnostic applications.

What is claimed is:

1. A method for calibrating a flow cytometry instrument for using said instrument to obtain at least one light-related signal from particles passing through the instrument for analysis comprising:

passing calibration particles, having characteristics of like nature to particles expected to be tested, in a liquid flow stream so that each calibration particle passes, substantially one at a time, through an incident beam of light;

detecting a light signal from the calibration particles passing through said beam of light;

detecting a noise signal from the calibration particles passing through said beam of light;

determining the ratio of the level of detected light signal to the level of detected noise signal;

reporting said ratio as a measured separation value between the light signal and the noise signal;

comparing said measured separation value to a predetermined separation value which represents a threshold for minimum instrument performance; and adjusting, if the predetermined separation value has not been attained, the operation of the instrument, while the calibration particles are passing therethrough, until the measured separation value reaches said predetermined separation value whereby the instrument is calibrated for subsequently analyzing particles.

2. The method of claim 1 wherein said calibration particles are substantially spherical beads.

3. The method of claim 2 wherein said beads have a diameter between 0.5 and 20 microns.

4. The method of claim 3 wherein the diameter of said beads is between 2 and 8 microns.

5. The method of claim 2 wherein said beads are made of plastic material.

6. The method of claim 5 wherein said plastic material is selected from the group of plastics consisting of styrene, acrylamide, propylene and vinylchloride.

7. The method of claim 1 wherein said calibration particles are chicken red blood cells.

8. The method of claim 1 wherein said calibration particles are capable of emitting fluorescence at a known wavelength and the light-related signal for which the instrument is to be calibrated is said known wavelength of fluorescence.

9. The method of claim 8 wherein said calibration particles are fluorescently-labeled osmiumtetraoxide-fixed chicken red blood cells.

10. The method of claim 1 wherein said calibration particles are capable of emitting fluorescence at a plurality of known wavelengths and the light-related signal for which the instrument is to be calibrated is each of the plurality of known wavelengths of fluorescence.

11. The method of claim 1 wherein said calibration particles are unlabeled so as to be substantially incapable of emitting fluorescence.

12. The method of claim 1 wherein said calibration particles are included in a mixture wherein two particle species are labeled with different fluorescence agents and another particle species is unlabeled so that two fluorescence signals are calibrated, said unlabeled particles serving as the medium to introduce a noise signal which is detected to establish the signal to noise ratio for each fluorescence signal.

13. The method of claim 12 wherein the adjusting step includes compensating each fluorescent signal by substantially eliminating spectral overlap.

14. The method of claim 13 wherein said compensating step includes electrically subtracting a proportion of the first fluorescent light signal from the second fluorescent light signal and electrically subtracting a proportion of the second fluorescent light signal from the first fluorescent light signal.

15. The method of claim 14 further including displaying the uncompensated fluorescence signals in a dot-population display wherein a first group of dots represents the first fluorescent light signal and a second group of dots represents the second fluorescent light signal.

16. The method of claim 15 wherein said dot population display includes a digital readout of compensation values for said first and said second fluorescent light signals, said adjusting step including the adjustment of the compensation values until a predetermined compensation value is reached for each fluorescent light signal whereby each fluorescent light signal is compensated.

17. The method of claim 12 wherein the fluorescently-labeled calibration particles and the unlabeled calibration particles are provided in substantially equal amounts in a carrier liquid which is used to form said liquid flow stream containing the calibration particles.

18. The method of claim 1 wherein said reporting step includes displaying said ratio in a form visible to an operator performing the calibration method.

19. The method of claim 18 wherein said reporting step includes displaying a histogram for the light signal being detected, said histogram showing the light signal mean channel and the noise signal mean channel.

20. The method of claim 19 wherein said reporting step includes displaying, in digital readout form, the value of the light signal mean channel, the value of the noise signal mean channel, the separation value between the light signal mean channel and the noise signal mean channel representing said signal to noise ratio, and said predetermined separation value representing said threshold for minimum instrument performance.

21. The method of claim 20 wherein said reporting step includes displaying a plurality of histograms, each for a different light-related signal being detected, and further displaying said digital readout values associated with each different histogram of light-related signals.

22. The method of claim 21 wherein said reporting step includes displaying three histograms and associated digital readout values for detecting three different light-related signals, two of said light signals being fluorescence at different wavelengths, the third signal being a light scatter signal.

23. The method of claim 1 wherein said reporting step expresses the ratio as a linearized difference between the light signal and the noise signal.

24. The method of claim 1 wherein the adjusting step includes adjusting detectors to positions which improve receipt of the respective signals which are detected.

25. A method for calibrating an instrument for using said instrument to obtain at least one light-related signal from particles under analysis comprising:
directing an incident beam of light at calibration particles having one or more known characteristics related to particles expected to be analyzed;
detecting a light signal from the calibration particles;
detecting a noise signal from the calibration particles;
measuring the ratio of the level of detected light signal to the level of detected noise signal and reporting same;
comparing said measured ratio to a predetermined ratio which represents a threshold for minimum instrument performance; and
adjusting, if the predetermined ratio has not been attained, the operation of said instrument, while the calibration particles are within the incident beam of light, until the measured ratio reaches said predetermined ratio whereby the instrument is calibrated for subsequently analyzing particles.

26. The method of claim 25 wherein said calibration particles include labeled particles and unlabeled particles, and wherein the detected light signal is associated with said labeled particles and the detected noise signal is associated with said unlabeled particles.

27. The method of claim 25 wherein said ratio is reported as a linearized separation value between the light signal and the noise signal.

28. A method for calibrating a flow cytometry instrument for using said instrument to obtain at least two different fluorescence signals from particles passing through the instrument for analysis comprising:
passing substantially spherical calibration beads in a liquid flow stream so that each bead passes, substantially one at a time, through an incident beam of light, said beads being labeled with two different fluorochromes and provided in substantially equal amounts in a carrier liquid which is used to form said flow stream;
detecting each of the two fluorescence signals from the beads passing through said beam of light;
detecting noise signals associated with each of the two fluorescence signals, the unlabeled beads providing the noise signal for each of the two fluorescence signals;
determining the ratio of the level of detected fluorescence signal to the level of detected noise signal for each of the two fluorescence signals;
displaying said ratio for each of the two fluorescence signals as a measured separation value between each respective light signal and the noise signal, said displaying step utilizing a log scale relationship in which the ratio of signal to noise is expressed by the mean channel linear difference between the light signal and the noise signal;
comparing said measured separation value for each of the two fluorescence signals to predetermined separation values each of which represents a threshold for minimum instrument performance; and
adjusting, if the predetermined separation values for either of the two fluorescence signals has not been attained, the operation of the instrument while the calibration beads are passing therethrough until each measured separation value reaches the predetermined separation value, whereby the instrument is calibrated for subsequently obtaining said two fluorescence signals from particles to be analyzed.

* * * * *